US 6,707,055 B2

(12) United States Patent
Vargas

(10) Patent No.: US 6,707,055 B2
(45) Date of Patent: Mar. 16, 2004

(54) METHOD AND APPARATUS FOR DETECTING PINHOLE DEFECTS IN A DIELECTRIC LAYER

(75) Inventor: Leroy C. Vargas, New Bedford, MA (US)

(73) Assignee: Polaroid Corporation, Waltham, MA (US)

( * ) Notice: Subject to any disclaimer, the term of this patent is extended or adjusted under 35 U.S.C. 154(b) by 193 days.

(21) Appl. No.: 09/967,202

(22) Filed: Sep. 28, 2001

(65) Prior Publication Data

US 2003/0062919 A1 Apr. 3, 2003

(51) Int. Cl.[7] .............................................. G01N 21/88
(52) U.S. Cl. ................... 250/559.4; 250/559.45
(58) Field of Search .................. 250/559.45, 559.4, 250/559.43, 559.27; 324/548, 554; 427/8–10

(56) References Cited

U.S. PATENT DOCUMENTS

| 864,785 A | 9/1907 | Horn | |
|---|---|---|---|
| 2,701,336 A | 2/1955 | Anderson | 324/54 |
| 4,420,497 A | * 12/1983 | Tickle | 438/466 |
| 4,914,395 A | 4/1990 | Hamada | 324/557 |
| 5,196,799 A | 3/1993 | Beard et al. | 324/557 |
| 5,844,406 A | 12/1998 | Gormley et al. | 324/71.3 |
| 6,204,669 B1 | 3/2001 | Beard et al. | 324/557 |

FOREIGN PATENT DOCUMENTS

| FR | 2 458 806 | 1/1981 |
|---|---|---|
| GB | 1 323 567 | 7/1973 |
| JP | 0312561 | 5/1991 |
| JP | 10-1231100 | 5/1998 |
| JP | 11 218523 A | 8/1999 |
| JP | 11-218523 | 8/1999 |

* cited by examiner

Primary Examiner—Que T. Le

(57) ABSTRACT

A system for detecting defects in a layer of dielectric material is disclosed. The disclosed system comprises a first electrode, on which the layer is placed, at least one second electrode oppositely spaced apart from the first electrode and oppositely spaced apart from, but not in contact with, the top surface of the layer. A voltage, that is at least equal to the breakdown voltage corresponding to the spacing between the first and second electrodes in the absence of the material layer, is applied across the first and second electrodes. The presence and characteristics, such as the location and the cross sectional area, of defects are detected as a function of the flow of electrical current from the first electrode to the at least one second electrode.

20 Claims, 5 Drawing Sheets

METHOD AND APPARATUS FOR DETECTING PINHOLE DEFECTS IN A DIELECTRIC LAYER

BACKGROUND OF THE INVENTION

1. Field of the Invention

The present invention relates to the detection of defects in films and protective barriers. More specifically, it relates to the detection of defects in a dielectric layer, such as a film or protective barrier.

2. Background Description

There are various applications in which the presence of small defects in a dielectric layer is not acceptable. For example, in the case of dielectric substrates that are used as a base for the coating of chemicals used in photography or used the production of storage media, the presence of small "pinhole" defects can lead to the defective coatings. In another application where the dielectric layer is used as a barrier material to ensure protection against biological particles (such as viruses) and toxic materials, the presence of defects, such as pinholes or tears, renders the barrier permeable to biological particles and toxic materials and inoperable as a protective barrier. In food packaging, when thin dielectric layers are used for packaging, the presence of pinholes can lead to food spoilage or contamination. For the above examples, as well as other situations, techniques to inspect dielectric layers for pinhole detection are needed.

The nature and size of the defects varies with the manufacturing methods used to produce the dielectric layer. For example, in the production of surgical gloves and other prophylactic items, a mold or mandrel is dipped into liquid stabilized latex. Defects are likely to be pinholes are tears. In the production of the base layer for photographic applications, physical anomalies arising from undisolved, unmelted clumps of material can serve as initiator sites for fractures in the extruding phase of the process. These fractures represent a source of defects. Both of the above type of defects will be hereinafter referred to as "pinholes".

The defects or pinholes in cases of interest can be smaller than those detectable by optical inspection methods. Several approaches have been proposed for testing protective barriers in order to detect defects such as pinholes or tears. In U.S. Pat. No. 5,196,799 (Beard et al., issued on Mar. 23, 1993) a method for testing protective barriers, such as surgical gloves and other prophylactic items, is disclosed. The method disclosed in U.S. Pat. No. 5,196,799 comprises measuring the resistive and reactivity impedance of the protective barrier in order to determine if defects are present.

In U.S. Pat. No. 6,204,669 (Beard et al., issued on Mar. 20, 2001), another method of detecting defects in barrier material is disclosed. Placing a conductive liquid or gas on one side of the protective barrier or layer and an ionized gas (plasma) on the other, changes in the conductivity of the liquid or gas caused by ionized gas particles that pass through the defects can be monitored as disclosed in U.S. Pat. No. 6,204,669. The methods of U.S. Pat. Nos. 5,196,799 and 6,204,669 monitor changes in bulk properties such as impedance and, therefore, can not provide information regarding the characteristics of the defects.

In two published Patent Abstracts of Japan, Publication No. 10-123100 (Yukitoshi et al., published on May 15, 1998) and No. 11-218523 (Hirosaku et al., published on Aug. 10, 1999), methods are described for detecting pinholes in insulating films. In 10-123100, in order to test a layer for pinholes, the dielectric layer is placed on one electrode and another electrode is placed in contact with the top surface of the layer. A high-voltage is applied between the two electrodes. Since the electrodes contact the layer, only slow relative movements of the layer are possible.

In Japanese Patent Publication No. 11-218523, another apparatus for detecting pinholes in a dielectric layer is described. The layer is placed on a roll electrode that also serves to transport the layer. A second electrode is brought close to or into contact with the top surface of the layer. When the layer is electrified, a signal is detected. In this invention, the two electrodes are also in close contact with the layer thereby limiting the transport speed of the layer.

The presently available systems for detecting pinhole defects in a dielectric layer do not provide the ability to transport the layer at arbitrary speeds while at the same time being able to observe the location and characteristics of the pinholes.

SUMMARY OF THE INVENTION

It is the primary object of this invention to provide a system for detecting pinhole defects in a dielectric layer that allows the transport of the layer at arbitrary speeds while at the same time allowing the determination of the location and characteristics of the pinholes.

To achieve this and other objects, a system for detecting defects in a layer of dielectric material, the defects being characterized by the absence of the dielectric material where the absence of dielectric material provides a continuous path across the layer, is disclosed. The disclosed system comprises a first electrode, on which the layer is placed, at least one second electrode oppositely spaced apart from the first electrode and oppositely spaced apart from, but not in contact with, the top surface of the layer. A voltage, that is at least equal to the breakdown voltage corresponding to the spacing between the first and second electrodes in the absence of the material layer, is applied across the first and second electrodes. The presence and characteristics, such as the location and the cross sectional area, of defects are detected as a function of the flow of electrical current from the first electrode to the at least one second electrode. In one embodiment, a resistor is connected in series with the voltage source and either the first electrode or the second electrode and the applied voltage is a DC (direct current) voltage. One embodiment of the means for detecting the presence and characteristics of defects comprises a gas discharge bulb connected in series between the resistor and the electrode to which the resistor was connected, and a photodetector receiving optical radiation emitted by the gas discharge bulb. The layer can be a continues web of a given width; in that embodiment, the first electrode is a metal cylindrical roll electrode having a roll width at least equal to the web width; means of transporting the web allow the translation of the web; and the second electrode is a brush electrode or a linear array of brush electrodes having a width substantially equal to the web width.

The system of this invention, in the embodiment in which the first electrode is a metal cylindrical electrode, can be utilized to inspect webs of dielectric material for pinhole defects in applications such as photographic film, packaging material, base material for magnetic storage media, dielectric wrap for preservation of food, and the general purpose dielectric wrap. In the embodiment in which the first electrode is a flat electrode, the system of this invention can be utilized to inspect dielectric layer such as those used in batteries, for example. In another embodiment in which the first electrode is a holder mandrel for surgical or protective gloves or in which the first electrode is a holder mandrel for other prophylactic items, the system of this invention can be utilized to inspect these protective or prophylactic items. Another applications of the system of this invention is the inspection of dielectric layers used in food packaging. While the above description refers to pinhole defects, it should apparent that larger defects can also be detected. It should also be apparent that the system of this invention can be utilized for inspection and defect identification in other applications in which a dielectric layer is used.

DESCRIPTION OF THE DRAWINGS

The novel features that are considered characteristic of the invention are set forth with particularity in the appended claims. The invention itself, however, both as to its organization and its method of operation, together with other objects and advantages thereof will be best understood from the following description of the illustrated embodiment when read in connection with the accompanying drawings wherein:

DETAILED DESCRIPTION

The present invention discloses a system and method for detecting pinhole defects in a dielectric layer that allows the transport of the layer at arbitrary speeds while at the same time allowing the determination of the location and characteristics of the pinholes. This object is accomplished by providing two electrodes: a first electrode on which the layer is placed and provides support for the layer, and a second electrode opposite to the first electrode and also opposite the top surface of the layer but not in contact with the layer. A voltage, of a magnitude large enough to cause breakdown of the ambient gas in the absence of a layer, is applied across these two electrodes. The presence of the dielectric layer prevents the breakdown of the ambient gas. When a pinhole defect appears, the insulating effect of the dielectric is absent and breakdown occurs in the ambient. The flow of current from one electrode to the other electrode gives rise to a detectable and measurable signal. This signal provides the means for determining the location and characteristics of the pinholes. This system and its corresponding method of operation are described in detail hereinafter.

Figure 1:
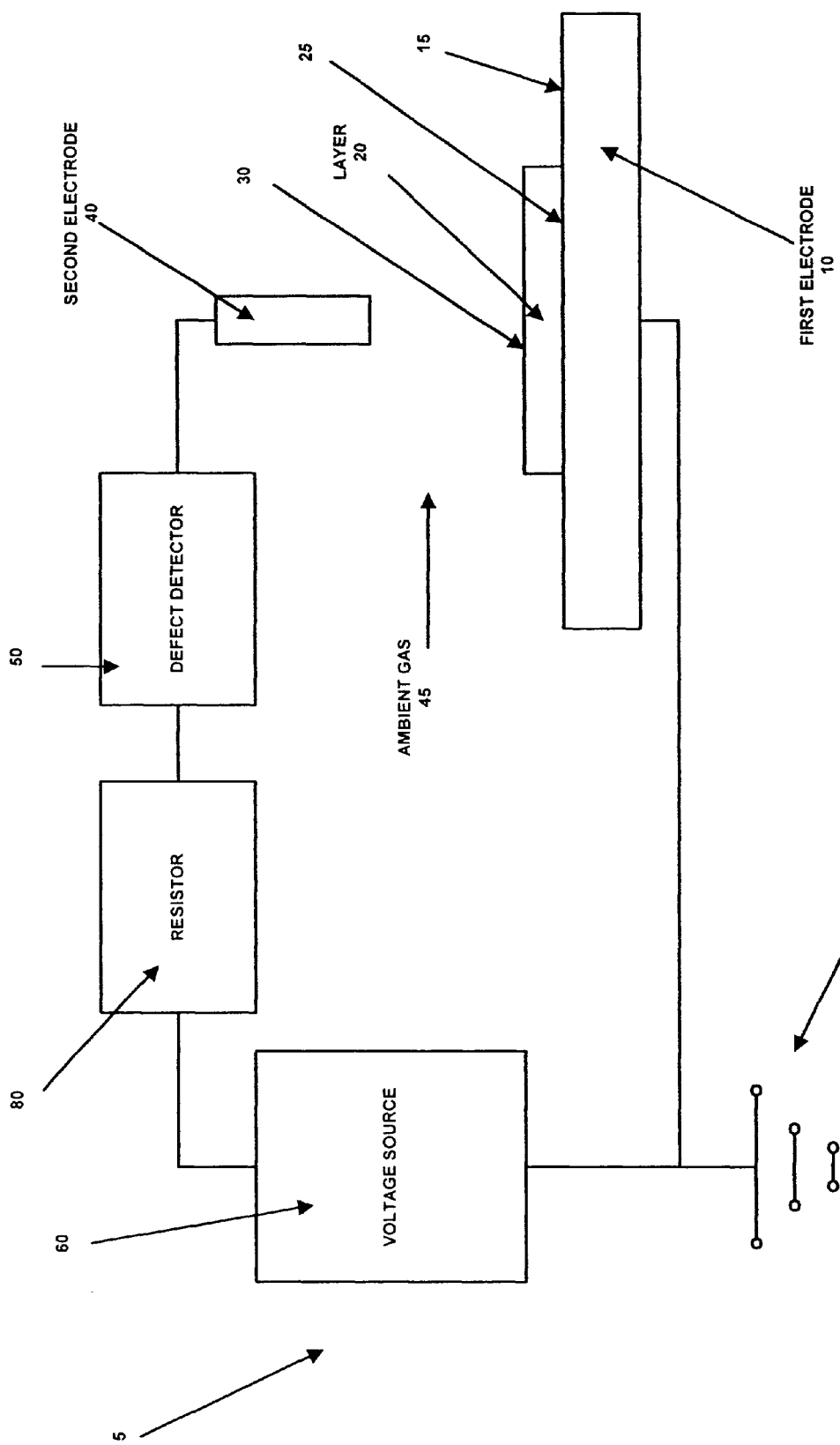
FIG. 1 depicts a block diagram of one embodiment of a system for detecting defects in a layer of dielectric material according to this invention.

Referring to FIG. 1, the system 5 is comprised of a first electrode 10 on which a layer of dielectric material 20 is supported, at least one second electrode 40, and a voltage source 60, providing a voltage between the two electrodes. A defect detector 50 is connected in series with the voltage source and either the first electrode or the second electrode. In the embodiment in which there is more than one second electrode 40, a defect detector 50 is connected in series with each second electrode 40. The first electrode 10 has a layer supporting surface 15 which is in contact with at least one point with the supported surface 25 of the layer 20. The second electrode 40 is oppositely spaced apart from the layer supporting surface 15 of the first electrode 10 and from the unsupported surface 30 of the dielectric layer 20. The dielectric layer 20 is disposed between the layer supporting surface 15 of the first electrode and the second electrode 40. The electrical connection between the voltage source 60 and the first electrode 10 and the second electrode 40 can be implemented by connecting the voltage source 60 to a ground connection 70 and the first electrode 10 to the ground connection 70. In one embodiment a resistor 80 is connected in series with the voltage source 60. The resistor 80 serves as a current limiting resistor so as to prevents possible damage to the dielectric layer 20. Since the system is not placed in a vacuum, ambient gas 45 fills the space between the first electrode 10 and the at least one second electrode 40. In many embodiments the ambient gas 45 is air. It should be apparent that in some embodiments other ambient gases can be used.

The output of the defect detector 50 is a function of the electrical current flowing between the voltage source 60 and the second electrode 40. In one embodiment, the defect detector 50 comprises a gas discharge bulb (52 in FIG. 3) connected in series between the voltage source 60 and the second electrode 40 and a photodetector (55 in FIG. 3) receiving optical radiation emitted by the gas discharge bulb 52. The above described embodiment off the defect detector 50, comprising a gas discharge bulb 52 and a photodetector 55, provides enough sensitivity to detect characteristics of the pinhole defects such as the defect area. Since the current flowing through the defect is proportional to the defect area, a measurement of the current or an effect caused by the current, such as the optical radiation from the gas discharge bulb 52, is a function of the defect area. In other embodiments, the defect detector 50 can be any one of the many ways of measuring current with enough sensitivity to discern the presence of defects.

Figure 2:
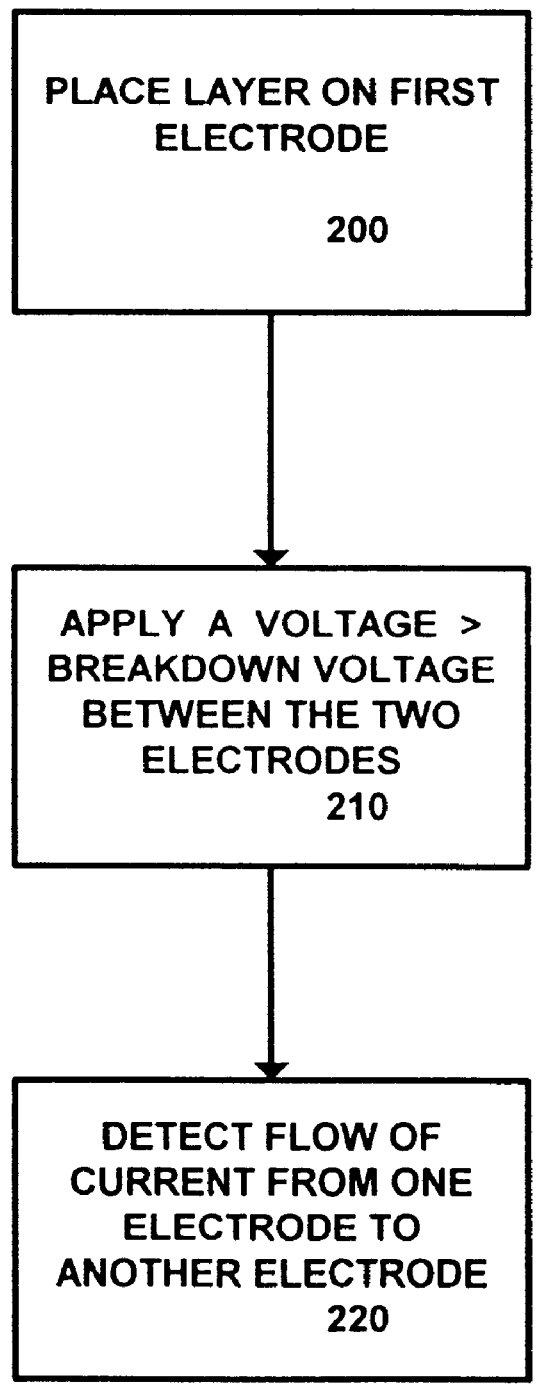
FIG. 2 depicts a flow chart of one embodiment of a method for detecting defects in a layer of dielectric material according to this invention.

A method of detecting defects in a dielectric layer is shown in FIG. 2. The layer is placed on the first electrode 10 (step 200, FIG. 2). The placement of the layer 20 can be performed manually, automatically (for example, by machine or robot), or can happen in the process of transporting a web (when the layer 20 is a continuous web). The first electrode 10 can be a flat plate, a mandrel designed such that it conforms to the layer (when the layer is of a specific geometry such as a glove or a prophylactic item), or a roll electrode (in the embodiment in which the layer is a continuous for web). A voltage is then applied across the first electrode 10 and the at least one second electrode 40 (step 210, FIG. 2). The applied voltage must be larger than or equal to the breakdown voltage in the ambient gas 45 in the absence of the layer 20.

The breakdown voltage in a given gas is a function of three parameters: the product of the electric field and a characteristic distance, the pressure of the gas times the characteristic distance, and the product of the pressure and the wavelengths of the electric field. An equivalent set of parameters are the product of the electric field and the characteristic distance, the ratio of the electric field to the pressure and the product of the pressure and the wavelengths of the electric field. (See S. C. Brown, Basic Data of Plasma Physics, pp. 148–151, 1959, M.I.T. Press, Cambridge, Mass.). For the DC breakdown only to parameters are required to specify the breakdown voltage since the wavelengths is equal to zero. Data on the required breakdown voltage for several gases (including air) and is available in the literature (See S. C. Brown, Basic Data of Plasma Physics, pp. 240–244, 1959, M.I.T. Press, Cambridge, Mass. and See S. C. Brown, Introduction to Electrical Discharges in Gases, Ch. 10 and Ch. 11, 1966, John Wiley and Sons, New York, N.Y.). Caution is advised in applying data for parallel plate electrodes to other electrodes since electrodes with sharp corners (or practically, small spherical tips) will produce more intense electric fields (see for example, J. D. Jackson, Classical Electrodynamics, $2^{nd}$ edition, pp. 75–78, 1975, John Wiley and Sons, New York, N.Y.).

The presence of the dielectric layer prevents breakdown in the ambient gas. When a pinhole is present, the pinhole provides a path through which electrical current can flow from the first electrode 10 to the second electrode 40. Thus, breakdown of the gas is possible in the presence of pinholes. Detecting the flow of current (and its magnitude) from one of the electrodes to the other electrode (step 220, FIG. 2) provides the means for detecting pinholes.

Details of one embodiment of this invention are given below.

Sample Embodiment

Figure 3:
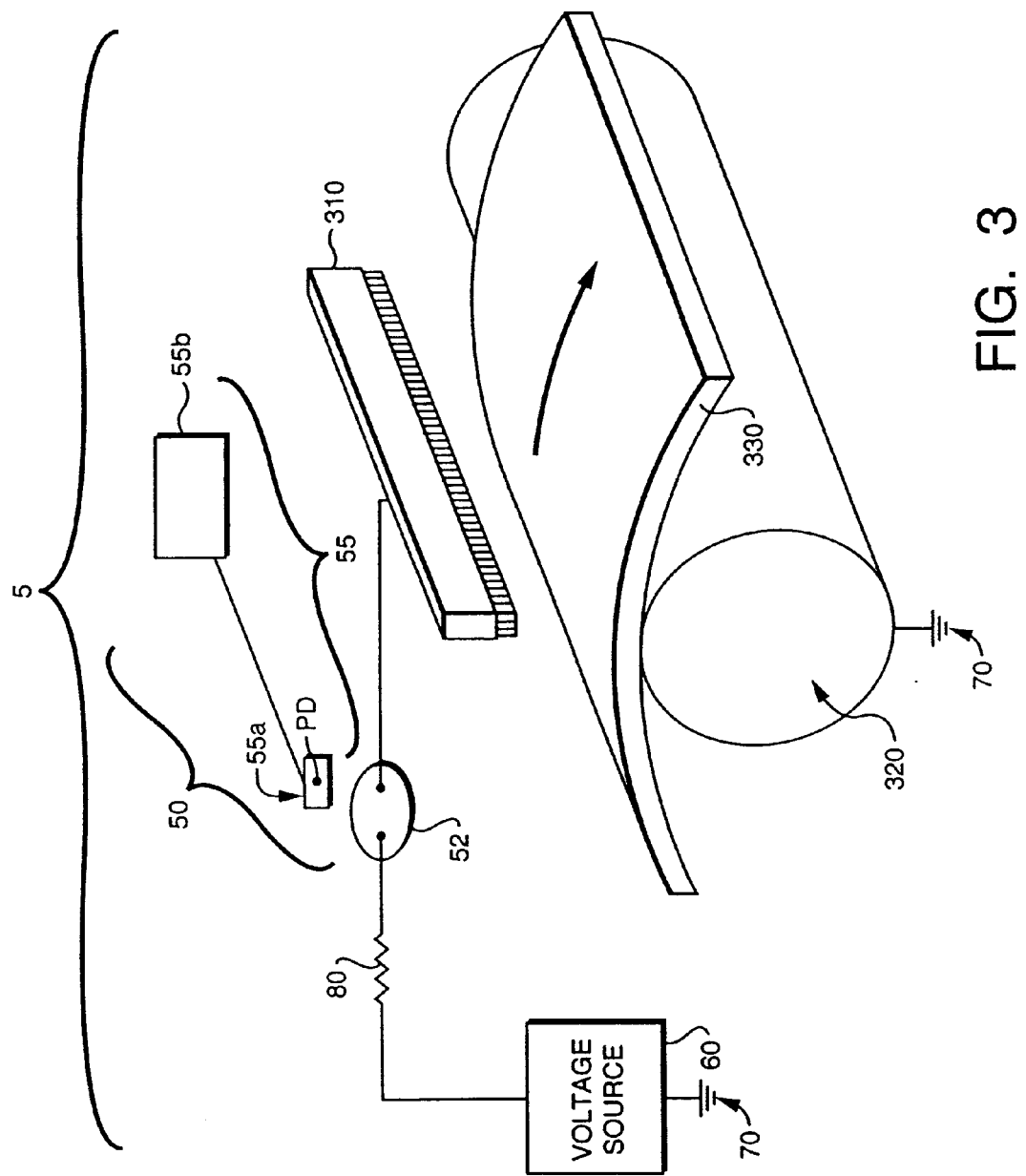
FIG. 3 is a graphical representation of the embodiment of the system for detecting defects in a layer of dielectric material according to this invention in which the layer is be a continues web of a given width and the first electrode is a metal cylindrical roll electrode having a roll width at least equal to the web width.

In FIG. 3, a specific embodiment in which the first electrode 10 is a roll electrode 320 and the dielectric layer 20 is a continuous web 330 of dielectric material is shown. The cylindrical roll electrode 320 has a roll width at least equal to the web width. The second electrode 40 is at least one brush electrode 310 having a width substantially equal to the web width. In determining the width of the at least one brush electrode 310, the fringing fields from the brush electrode 310 are taken into consideration so that the width of the entire web is subjected to an electric field capable of causing breakdown of the ambient gas 45. As will be readily understood there can be more than one brush electrode 310. The roll electrode 320 is connected to ground via a ground connection 70 and the voltage source 60 is also connected to ground. The ground connection 70 serves to connect the voltage source 60 through the roll electrode 320. The voltage source 60 is connected to the brush electrode 310 through a resistor 80 and a gas discharge bulb 52. The resistor 80 serves as a current limiting resistor and, thus, prevents possible damage to the web 330. Typical values of the resistor 80 range from 2 to 30 MegaOhms. The resistance 80 can be varied to accommodate various breakdown conditions of the ambient gas 45. The gas discharge bulb 52 is part of the defect detector 50. The defect detector 50 also comprises a photodetector 55. The photodetector 55 is comprised of a photodetector element 55a and a display or recorder 55b. A silicon photo diode can be used as the photodetector element 55a. Other choices for the photodetector element 55 are cadmium selenide (CdSe) cells or cadmium sulfide cells (CdS). The display or recorder 55b provides a record of the magnitude of the pinhole detection signal. It should be apparent that the display or recorder 55b can be connected to a computer, such as a personal computer, or can also comprise a personal computer or a special-purpose computer. Means of transporting the web (not shown) are usually included in a system such as that shown in FIG. 3. Such means for transporting the web are well-known in the art and are found, for example, in coating equipment and in web inspection equipment.

The system that provides the means for transporting the web can also provide timing information that can be used to synchronize with the recording of the pinhole detection data in order to provide pinhole position data along the web. Their web is transported at a constant velocity. With the presence of a fiducial mark, which can be generated in several different manners known to those skilled in the art (for example, a mark at the beginning of the tape, or a signal generated by the tape leader, or a signal generated by a photocell as the tape leader starts to be transported), a timing signal can be generated starting at a given point in the web. The combination of the web's constant transport velocity and the timing signal provides a measurement of distance. The pinhole detection data can be synchronized with the timing signal, thereby providing means for measuring the pinhole location along the web. The resolution of the determination of location of the defect the pans on the area of the second electrode 40 that participates in the discharge. The brush electrode 310 will provides a determination of the location of the pinhole within a given resolution; new electrodes will provide a determination of the location of the pinhole with a different resolution. It should be apparent that other systems, such as a system in which the letter 20 is stationary and the second electrode 40 is transported over the layer 20, can also provide the capability of determining pinhole location.

It should also be apparent that the at least one brush electrode 310 could be a linear array of brush electrodes. Such an array would provide the ability to determine the position of the pinholes in the cross web direction, if each brush electrode in the array had a pinhole detector connected in series with the electrode.

Figure 4:
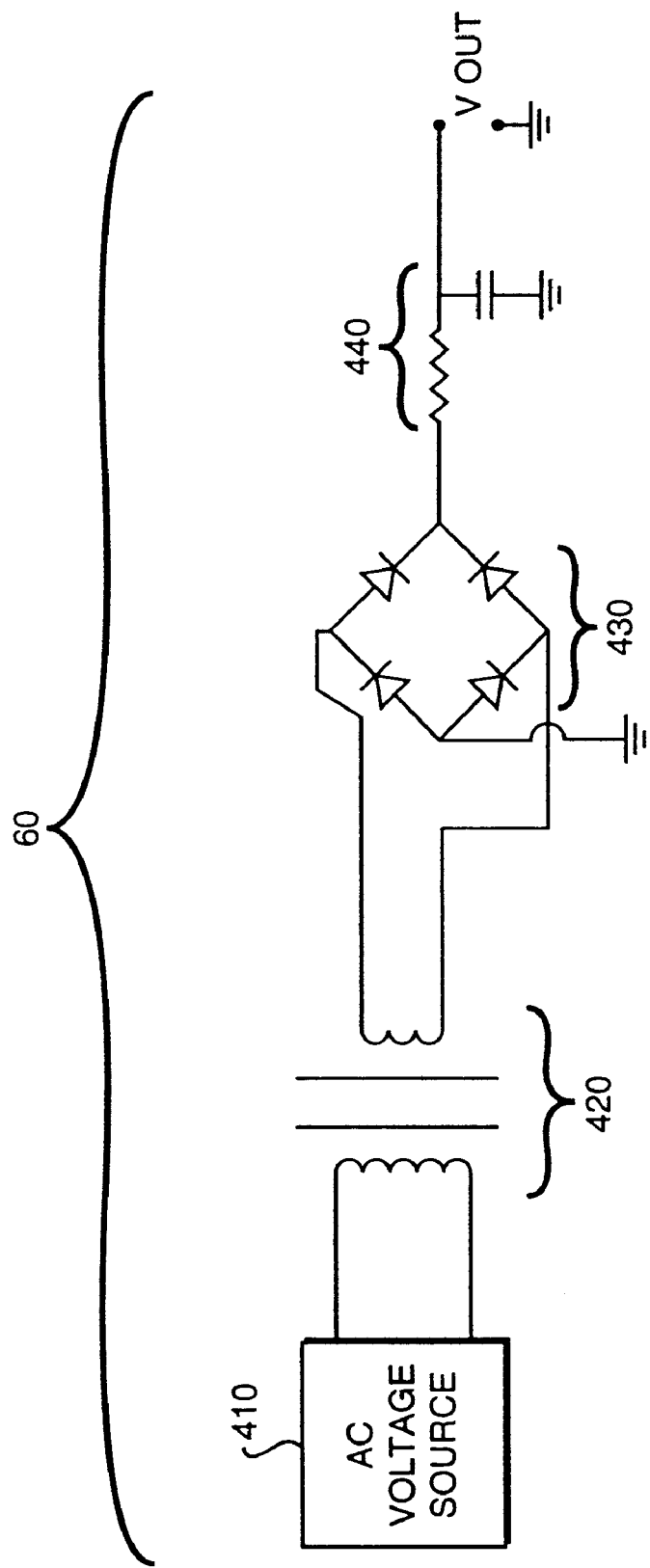
FIG. 4 is a graphical representation of an embodiment of a voltage source used in the system of this invention.

An embodiment of a DC voltage source 60 which can be used with the sample system described above is given in FIG. 4. An AC voltage source 410 is connected to the input of a step-up transformer 420 and the output of the transformer 420 is connected to the input of a full wave bridge rectifier 430. The output of the full wave bridge rectifier 430 is filtered by a filter 440. Typical values of output voltage range from 4.5 to 9 KV. Typical filter components are chosen to minimize ripple in a manner well known in the art.

Figure 5:
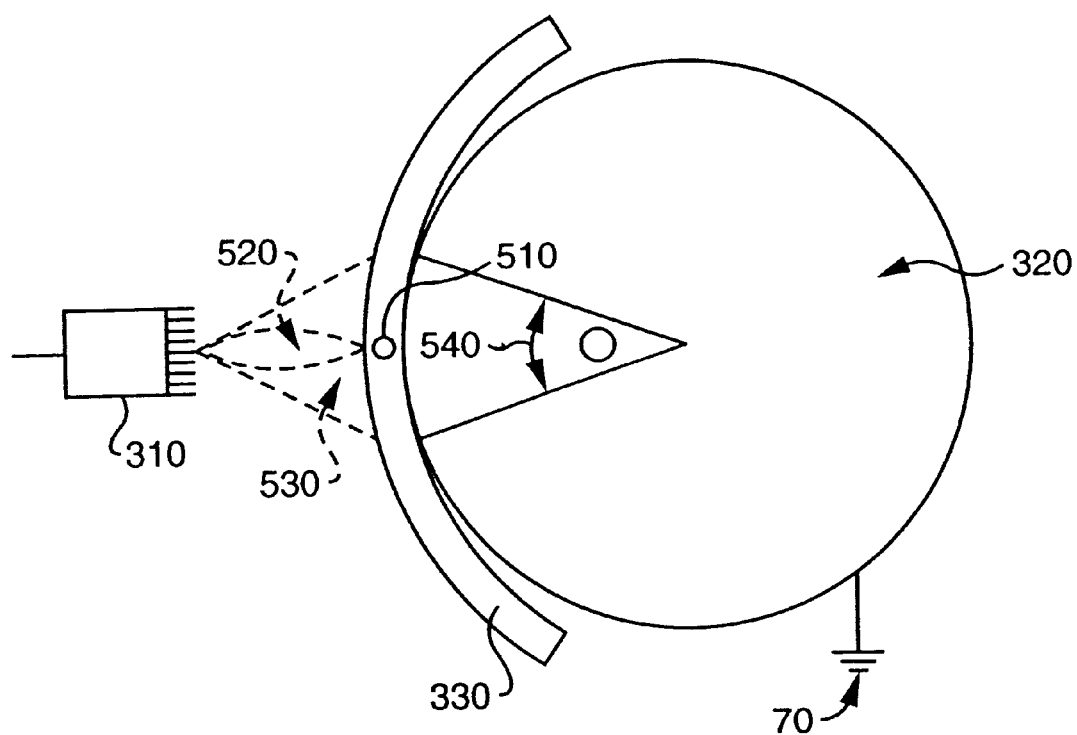
FIG. 5 is a graphical representation of a brush electrode as the second electrode utilized in the system of this invention in the embodiment depicted in FIG. 3.

The tips of brush electrodes produce more intense electric fields then would be obtained with parallel plate electrodes. The intense electric field makes ionization more likely. As shown in FIG. 5, once the air is ionized, since the electric field meets the ionization criterion over a wide area, labeled as a "cone of influence" 530, the conduction path will "follow" the pinhole defect 510. As in the defect moves out of the cone of influence 530, the ionization conditions are not met and the flow of current stops. This phenomenon has several advantageous consequences. It ensures that there is an extended opportunity to initiate conduction. These extended opportunity to initiate conduction allows higher web speeds. Defect detection for web speeds greater than 500 ft/min is possible. The increased length along the web transport direction also provides some resilience to variations in the magnitude of the output of the voltage source 70.

The system 5 can calibrated by means all of a web or dielectric layer that contains intentionally generated pinholes of known diameter. The system 5 is capable of detecting pinholes one micron or less in diameter.

Other Embodiments

If the first electrode is a mandrel such as that shown in U.S. Pat. No. 5,196,799, hereby incorporated by reference herein, (see FIG. 1 or FIG. 4 of U.S. Pat. No. 5,196,799) the second electrode or array of second electrodes can either conform to the first electrode or be scanned over the second electrode. These embodiment will allow the detection of pinhole defects and tears in surgical gloves or prophylactic items.

It should be apparent that other embodiments of a system for detecting pinholes are also possible within the scope of this invention. The dielectric layer could be stationary, supported by the first electrode 10, and the second electrode 40 could be scanned over the layer.

In other embodiments, the voltage source could be an AC voltage source. Also, it should be apparent that other methods of providing a relative displacement between the second electrode 40 could be used.

Thus, a system for detecting pinhole defects in a dielectric layer that allows the transport the layer at arbitrary speeds while at the same time allowing the determination of the location and characteristics of the pinholes has been disclosed.

Other embodiments of the invention, including combinations, additions, variations and other modifications of the disclosed embodiments will be obvious to those skilled in the art and are within the scope of the following claims.

What is claimed is:

1. An apparatus for detecting defects in a layer of dielectric material, said defects characterized by an absence of said dielectric material, where the absence of dielectric material provides a continuous path across the layer, said layer having a supported surface and an unsupported surface, said apparatus comprising:
    a first electrode, said first electrode having a layer supporting surface in contact with at least one point of the supported surface of the layer; and
    at least one second electrode oppositely spaced apart from the layer supporting surface of said first electrode and oppositely spaced apart from, the unsupported surface of said layer, said layer being disposed between the layer supporting surface of said first electrode and said second electrode; and
    means for applying a voltage across said first and second electrodes, said voltage being at least equal to the breakdown voltage corresponding to said spacing between the first and second electrodes in the absence of the layer of dielectric material; and
    means for detecting the presence and characteristics of defects, said
    means being responsive to variations of a flow of electrical current from said first electrode to the at least one second electrode.

2. The apparatus of claim 1 further comprising:
    a resistor electrically connecting said means for applying a voltage to said first electrode or said at least one second electrode.

3. The apparatus of claim 1 wherein the means for applying a voltage comprise a direct current (DC) voltage source.

4. The apparatus of claim 1 wherein the means for detecting the presence and characteristics of defects comprise:
    a gas discharge bulb electrically connecting said means for applying a voltage to said first electrode or said at least one second electrode; and
    a photodetector receiving optical radiation emitted by said gas discharge bulb.

5. The apparatus of claim 2 wherein the means for detecting the presence and characteristics of defects comprise;
    a gas discharge bulb electrically connecting said resistor to one of said first and second electrodes; and
    a photodetector receiving optical radiation emitted by said gas discharge bulb.

6. The apparatus of claim 1 wherein said layer is a continuos web of a given width, said first electrode is a cylindrical roll electrode having a roll width at least equal to the web width.

7. The apparatus of claim 1 wherein said at least one second electrode is at least one brush electrode.

8. The apparatus of claim 6 wherein said at least one second electrode is at least one brush electrode having a width substantially equal to the web width.

9. The apparatus of claim 6 wherein said at least one second electrode is a linear array of brush electrodes, said array having a width substantially equal to the web width.

10. The apparatus of claim 6 further comprising:
    means of transporting the web.

11. A method for detecting defects in a layer of dielectric material, said defects characterized by the absence of said dielectric material, where the absence of dielectric material provides a continuous path across the layer, one surface of said layer in contact with a layer supporting surface of a first electrode, an opposite surface of said layer spaced apart from at least one second electrode, said layer being disposed between the layer supporting surface of said first electrode and said at least one second electrode, said method comprising the steps of:
    applying a voltage across said first and said at least one second electrodes, said voltage being at least equal to the breakdown voltage corresponding to said spacing between the first and second electrodes in the absence of the layer of dilectric material; and
    detecting the presence and characteristics of said defects, said detection being responsive to variations of a flow of electrical current from said first electrode to the at least one second electrode.

12. The method of claim 11 wherein the applied voltage is a direct current (DC) voltage.

13. The method of claim 11 wherein the presence and characteristics of defects is detected by means comprising:
    a gas discharge bulb electrically connecting said means for applying a voltage to one of said first electrode or said at least one second electrode; and
    a photodetector receiving optical radiation emitted by said gas discharge bulb.

14. The method of claim 11 wherein said layer is a continuos web of a given width, said first electrode is a metal cylindrical roll electrode having a roll width at least equal to the web width.

15. The method of claim 11 wherein said second electrode is a brush electrode.

16. The method of claim 14 wherein said second electrode is a brush electrode having a width substantially equal to the web width.

17. The method of claim 14 wherein said at least one second electrode is a linear array of brush electrodes, said array having a width substantially equal to the web width.

18. The method of claim 14 further comprising the step of:
    transporting the web.

19. The method of claim 11 further comprising the step of:
    identifying the location of the defect.

20. The method of claim 11 further comprising the step of:
    determining the size of the defect.

* * * * *